US00PP22449P3

(12) United States Plant Patent
Clark

(10) Patent No.: US PP22,449 P3
(45) Date of Patent: Jan. 10, 2012

(54) BLACKBERRY PLANT NAMED 'APF-45'

(50) Latin Name: ***Rubus* subgenus *Rubus* Watson**
Varietal Denomination: APF-45

(75) Inventor: John Reuben Clark, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 12/802,283

(22) Filed: Jun. 3, 2010

(65) Prior Publication Data

US 2011/0302680 P1 Dec. 8, 2011

(51) Int. Cl.
*A01H 5/00* (2006.01)

(52) U.S. Cl. ..... Plt./203

(58) Field of Classification Search ..... Plt./203
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark et al. |
| PP11,865 | P2 | 5/2001 | Clark et al. |
| PP14,935 | P2 | 6/2004 | Clark |
| PP16,989 | P3 | 8/2006 | Clark et al. |
| PP17,162 | P3 | 10/2006 | Clark et al. |
| PP17,983 | P2 | 9/2007 | Cabrera Avalos |
| PP20,891 | P3 | 3/2010 | Clark |

OTHER PUBLICATIONS

Clark, J.R., et al., "'APF-45' primocane-fruiting blackberry," Hort, Science (2011) 46(4):670-673.

*Primary Examiner* — June Hwu
(74) *Attorney, Agent, or Firm* — Andrus, Sceales, Starke & Sawall, LLP

(57) ABSTRACT

Description and specifications of a new and distinct blackberry cultivar named 'APF-45' which originated from seed produced by a hand pollinated cross of Ark. Selection APF-1 (non-patented, unreleased genotype)×APF-12 (U.S. Plant Pat. No. 16,989) is provided. This new blackberry cultivar can be distinguished by its very firm fruit with excellent postharvest handling potential, medium-large size, attractive fruit appearance, very good flavor, excellent plant health, and cane erectness.

4 Drawing Sheets

Latin name: *Rubus* subgenus *Rubus* Watson.

BACKGROUND

The new cultivar of blackberry called 'APF-45' is described herein. The new cultivar originated from a hand-pollinated cross of Ark. Selection APF-1×APF-12 made in 2000. The seeds resulting from this controlled hybridization were germinated in a greenhouse in the spring of 2001 and planted in a field near Clarksville, Ark. (West-Central Arkansas). The seedlings fruited in the summer of 2002 and one seedling, designated APF-45, was selected for its very firm fruit with excellent postharvest handling potential, medium-large size, attractive fruit appearance, very good flavor, excellent plant health, and cane erectness.

SUMMARY OF THE INVENTION

The new and distinct cultivar of blackberry originated from a hand-pollinated cross of Ark. Selection APF-1 (non-patented, unreleased genotype; female)×APF-12 (U.S. Plant Pat. No. 16,989; male) made in 2000 and located near Clarksville, Ark. (West-Central Arkansas). The botanical designation of the new cultivar of blackberry is *Rubus* subgenus *Rubus* Watson.

The seeds resulting from this controlled hybridization were germinated in a greenhouse in the spring of 2001 and planted in a field near Clarksville, Ark. The seedlings fruited in the summer of 2002 on floricanes and one seedling, designated APF-45, was selected for its very firm fruit with excellent postharvest handling potential, medium-large size, attractive fruit appearance, very good flavor, excellent plant health, and cane erectness. Its primocane-fruiting habit was confirmed later that summer by observing primocane flowers.

During 2002, the original plant selection was propagated asexually from root cuttings at the above-noted location, and a test row of 40 plants was established. Subsequently, larger test plantings have been established with asexually multiplied plants at two locations in Arkansas. Additionally, the cultivar has been tested at test plots in Baxley, Ga., Lincolnton, N.C., Watsonville, Calif., and Aurora, Oreg., and at each location propagation was from root cuttings from the Clarksville, Ark. test plot.

The new cultivar has been asexually multiplied annually since 2002 by the use of root cuttings and by rooting adventitious shoots from root cuttings. It forms new shoots from adventitious buds on root cuttings readily. During all asexual multiplication, the characteristics of the original plant have been maintained and no aberrant phenotypes have appeared.

Test plantings over a wide geographic area have shown this new cultivar to be adapted to differing soil and climatic conditions. Further, its primocane fruiting performance is substantially better in more moderate summer climates such as Aurora, Oreg. and Watsonville, Calif., as evidenced by larger fruit weight and higher yields compared to Clarksville, Ark. A key differentiation of the new cultivar and its parents is that the primocane-fruiting plant produces fruit on current-season canes (primocanes), and the portion of the cane that does not fruit in the current season will fruit the following season (floricane fruiting). The cultivar differs from most blackberry cultivars which are floricane fruiting.

BRIEF DESCRIPTION OF THE PHOTOGRAPHS

The accompanying photographs show typical specimens of the new variety in color as nearly true as it is reasonably possible to make in a color illustration of this character.

DETAILED DESCRIPTION OF THE NEW CULTIVAR APF-45

Figure 1:
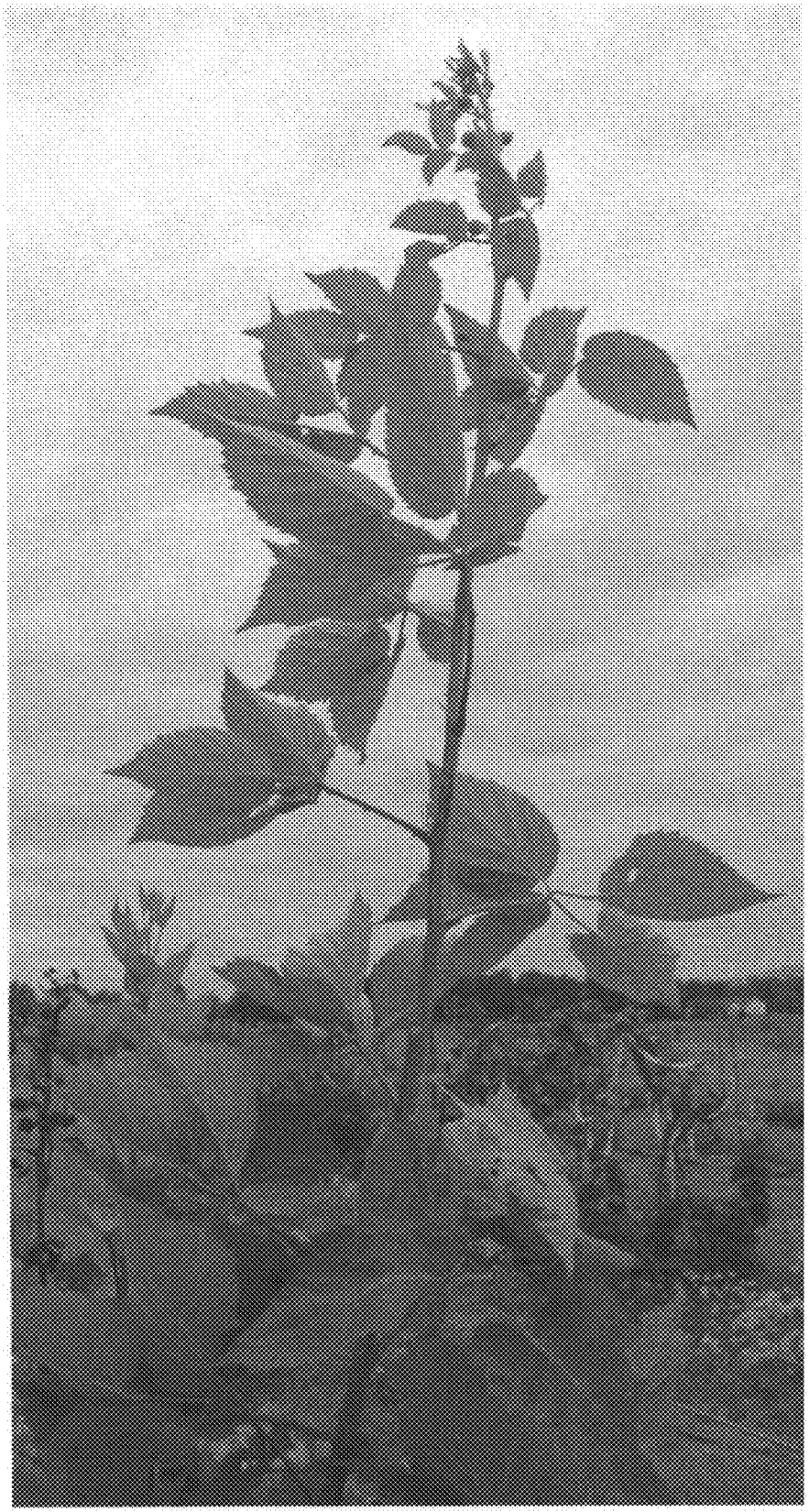
FIG. 1 is a photograph a blackberry cane of 'APF-45' in late June showing the primocane-fruiting character, as exemplified by flower buds at the terminus of a primocane taken near Clarksville, Ark.
Figure 2:
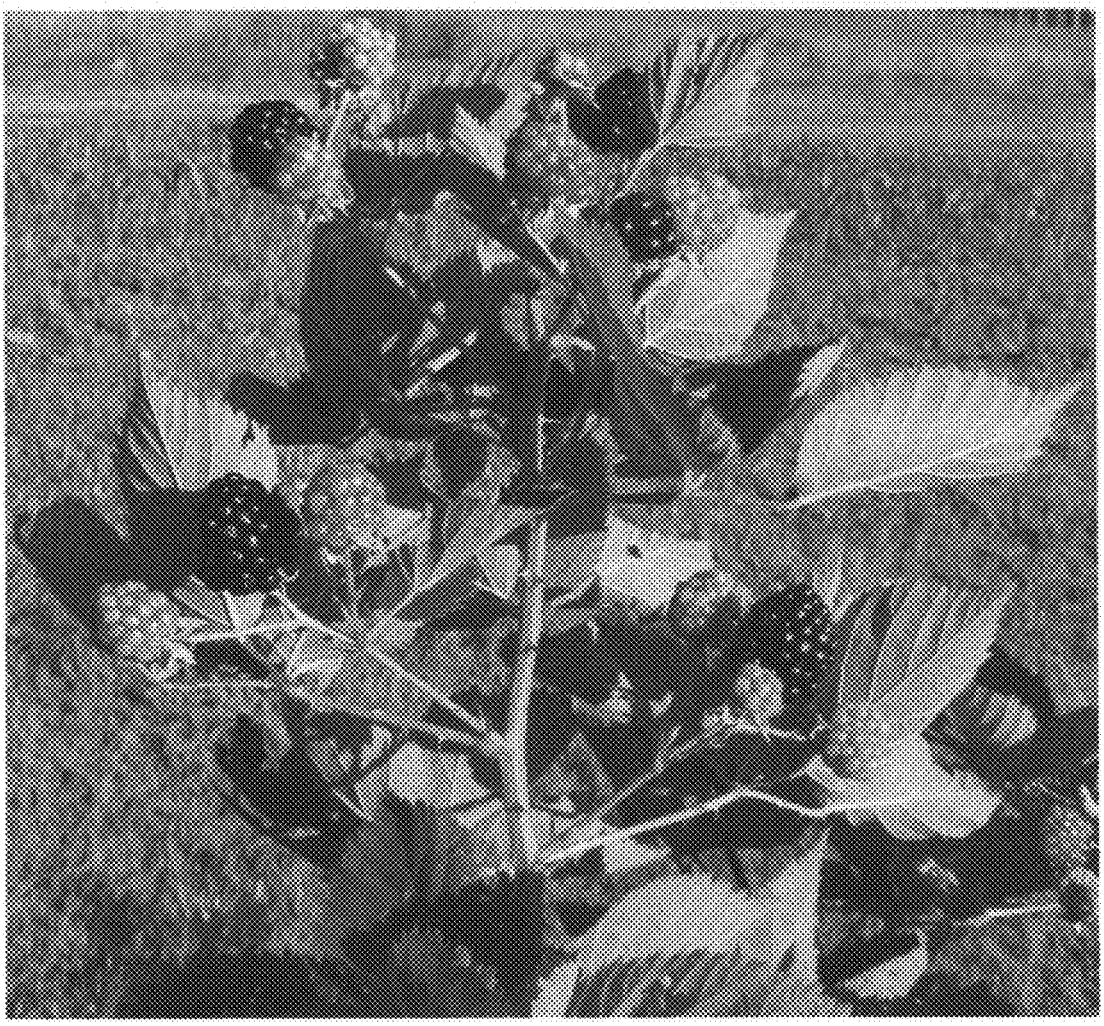
FIG. 2 is a photograph of ripe fruit on a primocane taken in late July near Clarksville, Ark.
Figure 3:
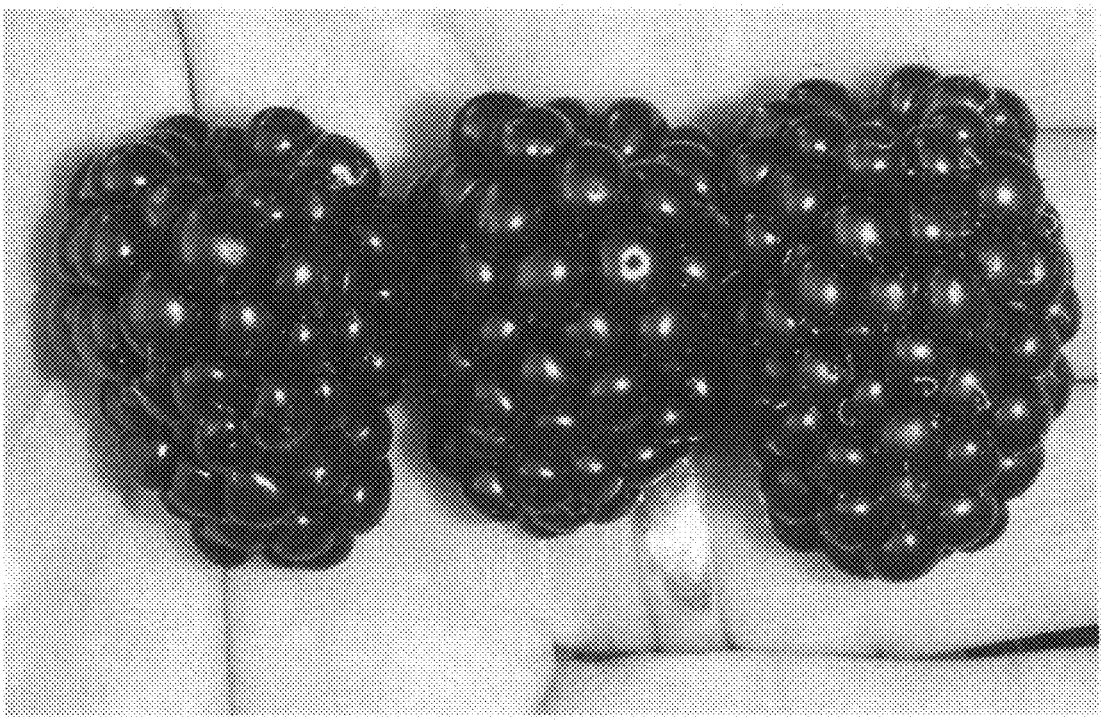
FIG. 3 is a photograph of floricane fruit taken in June, near Clarksville, Ark.
Figure 4:
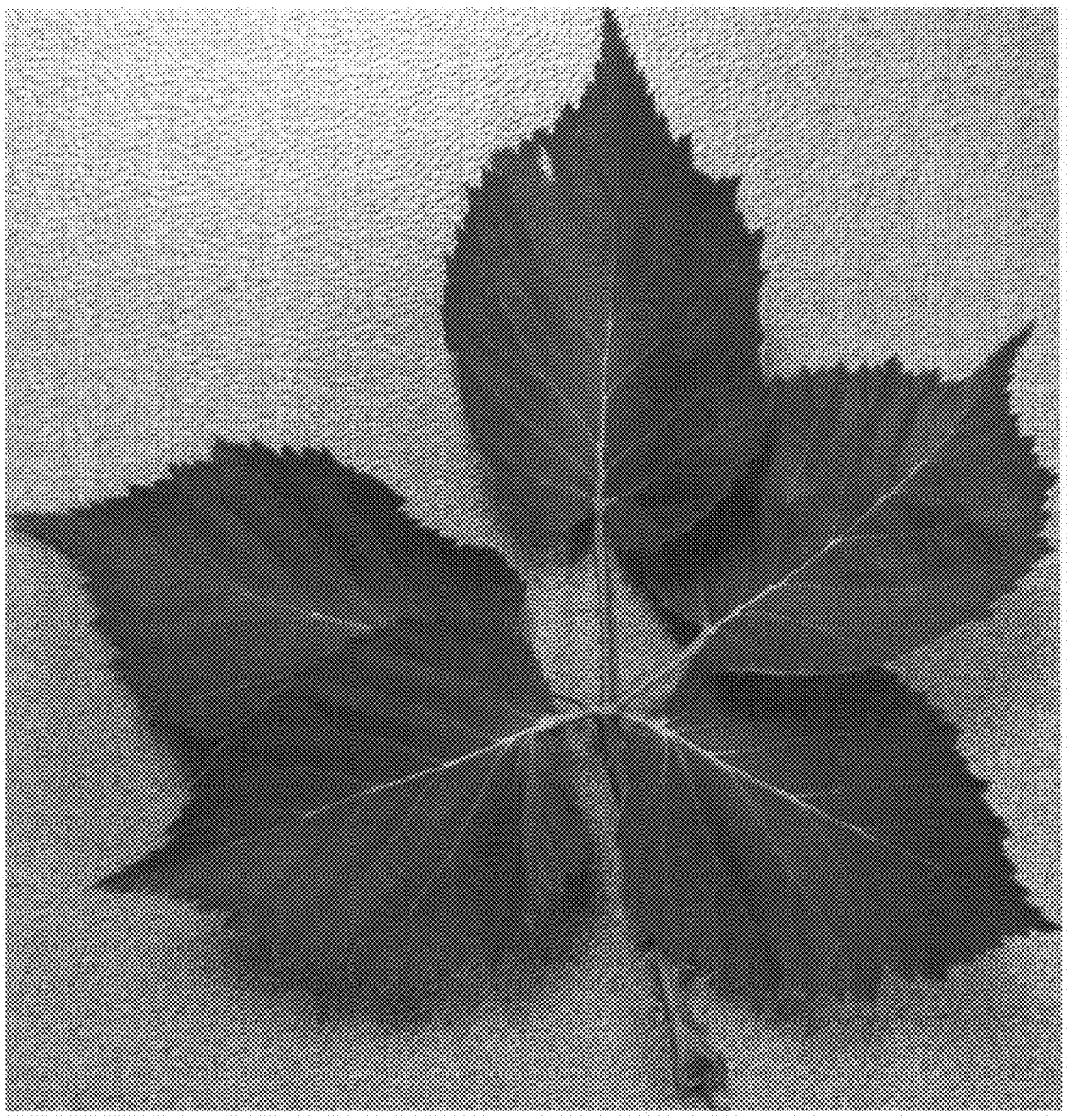
FIG. 4 is a photograph showing the adaxial side of a primocane leaf.

Plants and fruit of this new cultivar differ phenotypically from its parents. The new cultivar is more productive and has more erect canes than the parent APF-1, and has larger fruit and later ripening than parent APF-12. The new cultivar has much firmer fruit that has much better flavor than either of the parent blackberries. Although blackberries (*Rubus* subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes can be trained to a self-supporting hedgerow although it is beneficial to use a trellis with supporting wires to prevent canes from falling over due to wind or heavy fruit-loads. The plants are thorny. Plants and fruit are moderately resistant to anthracnose [*Elsinoe veneta* (Burkh.) Jenkins], and plants appear immune to orange rust [*Gymnoconia nitens* (Schwein.) F. Kern and H. W. Thurston.]. No screening has been done for resistance to double blossom/rosette [*Cercosporella rubi* (Wint.) Plakidas]

The floricane bloom period of the new cultivar begins on the same date and averages the same length as APF-12 and primocane bloom period begins two weeks later and can extend longer than APF-12 depending on temperatures during the priomcane bloom period.

Floricane fruit of the new cultivar begins ripening 4 days later than APF-12 and extends 10 days later than APF-12. Average first ripening date is June 9 in West-Central Arkansas. The average floricane fruiting period is 35-40 days. Average first primocane fruit ripening date is Aug. 8 in West-Central Arkansas. In Aurora, Oreg., first primocane fruit ripening date averaged Sep. 13.

Fruit yields of the new cultivar on floricanes are usually 3 to 4 kg (6 to 9 lb/plant) if the floricanes are retained for fruiting, exceeding that for APF-12, in West-Central Arkansas. Fruit yields of the cultivar on primocanes in West-Central Arkansas range from 0.2 to 1.8 kg (0.5 to 2.6 lb/plant) and exceed that of APF-12. On primocanes in Aurora, Oreg., yield averaged 4.4 kg (9.7 lb/plant), and in Watsonville, Calif. averaged 3.4 kg (7.5 lb/plant). The difference in primocane yields are believed to be due to temperatures in Oregon and California test locations being more moderate during primocane flowering and fruiting compared to West-Central Arkansas.

The fruit is elongated to blocky to slightly conical in shape, bright glossy black in color, and very attractive. The floricane fruit is medium-large (6-7 g) and 1.5 g larger than that of APF-12. Floricane fruit size of the new cultivar is maintained well throughout the entire harvest season. Primocane fruit in West-Central Arkansas of the new cultivar ranged from 4.3 to 5.2 g/berry, while primocane fruit in Aurora, Oreg. averaged 8.9 g and in Watsonville, Calif. averaged 7.2 g. Primocane fruit size in West-Central Arkansas can be reduced in high summer temperatures (exceeding 85 to 90° F.) but is more uniform in the Oregon and California test sites. The new cultivar exhibits excellent fruit fertility with full drupelet set. The fruit is very firm at maturity, comparable to that of Ouachita (U.S. Plant Pat. No. 17,162) and Natchez (U.S. Plant Pat. No. 20,891) and firmer than that of APF-12. Storage potential of fresh fruit of the new cultivar is comparable to that of Ouachita and Natchez and exceeds that of APF-12 cultivars.

The fresh fruit rates very good in flavor, comparable to Ouachita and Natchez cultivars and higher than APF-12. The flavor is sweet and mildly acidic, with a distinct blackberry aroma. The soluble solids concentration averages 9.7% on shiny black fruit, higher than APF-12 (9.1%) and lower than Ouachita (10.4%).

Floricane fruit and flower clusters are medium-large, cymose, and are mostly borne on the periphery of the plant canopy, providing easy access to harvest. Flower fertility is high and clusters are well filled.

Primocane fruit and flowers are borne on the cane terminus, and fruiting continues down the primocane during the season. Canes usually attain a length of 4.5 to 5.0 ft prior to the appearance of flower buds. The number of nodes down the cane that develop flowers is largely dependent on the length and conditions of the late summer to fall growing period.

The following is a detailed description of the botanical and pomological characteristics of the subject blackberry. Color data are presented in Royal Horticultural Society Colour Chart (1986 2$^{nd}$ edition) designations. Where dimensions, sizes, colors, and other characteristics are given, it is to be understood that such characteristics are approximations of averages set forth as accurately as practicable.

Plants used for botanical data were three years old and grown on a fine sandy loam soil with trickle irrigation at the Fruit Research Station near Clarksville, Ark. The plants were fertilized near budbreak (late March on average) with complete or nitrogen fertilizer, and had an additional nitrogen fertilizer application in early July. Primocanes were tipped at approximately 45 inches, and grown in a hedgerow training system. Weeds were controlled with pre- and postemergence herbicides supplemented with mechanical weed control activities. A single application of liquid lime sulfur was applied to the plants at budbreak, but no other fungicides were used. The descriptions reported herein are from specimens grown near Clarksville, Ark. unless otherwise noted.

Plant

Size: Plants are grown in a hedgerow and primocanes tipped at approx. 45-55 inches; plants in this system then range in size from approx. 45-55 inches tall and 36-40 inches wide.

Growth habit: Moderate vigor, canes erect; suckers from crown and roots.

Growth rate: Primocanes reach tipping height (107 cm) on June 1, approximately one month after emergence.

Productivity:

*Floricane.*—3 to 4 kg (6-9 lb/plant), higher than APF-12 (U.S. Plant Pat. No. 16,989).

*Primocane.*—0.2 to 1.8 kg (0.5-2.6 lb/plant), higher than APF-12; At Aurora, Oreg. 4.4 kg (9.7 lb/plant) and Watsonville, Calif. 3.4 kg (7.5 lb/plant).

Cold hardiness: Hardy to 8° (−13° C.) or lower comparable to slightly hardier than APF-12. The low temperature of 8° F. was the lowest the cultivar has been exposed to and fruited successfully after this exposure.

Canes: Thorny, erect.

*Floricane* (*dormant or winter cane*).—Cane diameter: base 1.95 cm; midpoint 1.23 cm; terminal 0.99 cm. Internode length: base 6.90 cm; midpoint 5.72 cm; terminal 4.31 cm. Floricane color: base Red-Purple Group (60C); midpoint Green Group. (143A); terminus Green Group (138 B) over Yellow-Green Group (146C). Thorn-density (per 30 cm of cane length): base 96.7; midpoint 43.6; terminus 34.9. Thorn length (from tip of thorn to bottom of thorn base): 6.0 mm, with non-curved thorn.

*Primocane* (*current-season cane*).—Cane diameter: base 1.45 cm; midpoint 0.97 cm; terminal 0.32 cm. Internode length: base 6.98 cm; midpoint 7.18 cm; terminal 1.02 cm. Primocane color: base Green Group (147C) over Green Group (146D); midpoint Green Group (146C); terminus Green Group (146C). Thorn density (per 30 cm of cane length): base 35; midpoint 23.7; terminus 19.7. Thorn length (from tip of thorn to bottom of thorn base): 5.8 mm, with retrosely barbed thorn. Date of primocane emergence: May 5.

Disease resistance: Moderate resistant to anthracnose, and plants appear immune to orange rust. No screening has been done for resistance to double blossom/rosette.

Foliage

Primocane:

*Leaves.*—Large; mature compound leaf width 20.82 cm; length 22.14 cm.

*Leaflet.*—Width 15.88 cm; length 16.53 cm; shape ovate with acuminate apex and cordate base; margin doubly serrated, serration teeth length 0.30 cm and width 0.29 cm; pubescence is very light on abaxial and adaxial surfaces; number of leaflets per compound leaf 5.

*Color.*—Base abaxial Yellow-Green Group (146B); adaxial Green Group (137A); midpoint abaxial Yellow-Green Group (146B); adaxial Green Group (137A); terminal abaxial Yellow-Green Group (146B); adaxial Green Group (137A).

*Petioles.*—Length: 11.95 cm; color: Yellow-Green Group (146D); texture smooth.

*Petiolules.*—Length: 3.98 cm; color: Yellow Green Group (146D); texture smooth.

*Stipules.*—Length: 1.86 cm; width: 0.24 cm; texture smooth.

Floricane:

*Leaves.*—Medium; mature compound leaf width 9.32 cm; length 11.52 cm.

*Leaflet.*—Width 6.44 cm; length 8.02 cm; shape ovate with acuminate apex and rounded base; margin serrated, with serration teeth length 0.42 cm and width at base 0.73 cm; pubescence is present on abaxial side only and infrequently. Number of leaflets per compound leaf is 3 most commonly but occasionally up to 5.

*Color.*—Base abaxial Yellow-Green Group (146B); adaxial Green Group (137A); midpoint abaxial Yellow-Green Group (146B); adaxial Green Group (137A); terminal abaxial Yellow-Green Group (146B); adaxial Green Group (137A).

*Petioles.*—Length 3.34 cm; color: Yellow-Green Group (146C); texture: smooth.

*Petiolules.*—Length 0.65 cm; color: Yellow-Green Group (146C) ; texture: smooth.

*Stipules.*—Length 0.83 cm; width: 0.16 cm: texture: smooth.

Flowers

Floricane:

*Date of bloom.*—10% bloom April 29; 50% bloom May 2; last bloom June 1, the same as APF-12.

*Petal color.*—White Group (155D).

*Reproductive organs.*—Stamens — erect, numerous. Pistils — numerous. Pollen — normal, fertile, and abundant.

*Flower diameter.*—3.68 cm.

*Petal size.*—Length 1.95 cm; width 1.23 cm.

*Average number flowers per cluster.*—8.25.

*Average number of petals per flower.*—5 to 6.

*Number of sepals per flower.*—5 to 6.

*Peduncle length.*—2.4 cm.

*Peduncle color.*—Yellow-Green Group (144A).

*Cyme type.*—Elongate simple cyme.

*Cyme* (*flower cluster*) *length.*—ave 107.0 mm but can extend up to 157.8 mm.

Primocanes:

*Date of bloom.*—First bloom 30 June, and can extend until frost depending on environment and cultural management, 14 days later than APF-12.

*Petal color.*—White Group (155D).

*Reproductive organs.*—Stamens — numerous. Pistils — numerous. Pollen — fertile and abundant unless temperatures exceed 85 to 90° F. where pollen production can be reduced.

*Flower diameter.*—3.75 cm.

*Petal size.*—Length: 2.0 cm; width: 1.5 cm.

*Average number flowers per cluster.*—15 but can vary depending on environment.

*Average number of petals per flower.*—5.

*Number of sepals per flower.*—5 to 6.

*Peduncle length.*—2.6 cm.

*Peduncle color.*—Yellow-Green Group (144A).

*Cyme type.*—Elongate simple cyme.

*Cyme* (*flower cluster*) *length.*—110.1 mm but can extend up to 170.2 mm.

Fruit

Floricane:

*Maturity.*—Average first ripe date June 9, 4 days after APF-12; with a fruiting period of 35-40 days.

*Size.*—Medium-large, average 6-7 g.

*Diameter of fruit at primary position on inflorescence.*—Equator 2.11 cm; base pole 1.86 cm; terminal pole 1.37 cm.

*Diameter of fruit at secondary positions on inflorescence.*—Equator 1.98 cm; base pole 1.63 cm; terminal pole 1.12 cm.

*Length* (*primary fruit*).—2.85 cm.

*Shape.*—Elongated to blocky to slightly conical.

*Color.*—Black Group (202A).

*Drupelet size.*—0.44 cm.; number per fruit 70-85 and can be more on larger fruit as number varies with fruit size.

*Seed* (*drupe*).—Average length 3.7 mm; width 2.1 mm; dry weight 4.5 mg; color dry Greyed-Orange (164B).

*Soluble solids.*—9.7%.

*pH.*—3.36.

*Acidity.*—0.52 g/100 ml expressed as citric acid.

*Processed quality.*—Not evaluated for processing.

*Uses.*—Fresh market use for shipping is the primary market due to excellent postharvest handling capability, but can also be used for other fresh market use including local sales.

Primocane:

*Maturity.*—Average first ripe date is Aug. 8 and can fruit until frost depending on environment and cultural management, 23 days later than APF-12; in Aurora, Oreg., first ripe date Sep. 13 with fruiting extending until mid October or later depending on temperature; in Watsonville, Calif. first ripe date Aug. 20 and fruiting extending until early December.

*Size.*—Medium, 4-5 g, 1 to 1.5 g larger than APF-12; In Aurora, Oreg. average size 8.9 g and in Watsonville, Calif. 7.2 g.

*Diameter of fruit at primary position on inflorescence.*—Equator 2.10 cm; base pole 2.13 cm; terminal pole 1.64 cm.

*Diameter of fruit at secondary positions on inflorescence.*—Equator 1.92 cm; base pole 1.90 cm; terminal pole 1.61 cm.

*Length* (*primary fruit*).—2.92 cm.

*Shape.*—Elongated to blocky to slightly conical.

*Color.*—Black Group (202A).

*Drupelet size.*—0.47 cm.

*Soluble solids.*—9.9%.

*pH.*—3.36.

*Acidity.*—0.51 g/100 ml expressed as citric acid.

*Processed quality.*—Not evaluated in processing.

*Uses.*—Fresh market use for shipping is the primary market due to excellent postharvest handling capability, but can also be used for other fresh market use including local sales.

The Cultivar

The most distinctive features of the cultivar are firm fruit with excellent postharvest handling potential, medium-large size, attractive fruit appearance, very good flavor, excellent plant health, and cane erectness.

I claim:

1. A new and distinct cultivar of blackberry plant named 'APF-45,' substantially as illustrated and described.

* * * * *